(12) United States Patent
Moenkemoeller (10) Patent No.: US 10,488,313 B2
(45) Date of Patent: Nov. 26, 2019

(54) PARTICLE SENSOR

(71) Applicant: Ralf Moenkemoeller, Bielefeld (DE)

(72) Inventor: Ralf Moenkemoeller, Bielefeld (DE)

(73) Assignee: PARAGON AG, Delbrueck (DE)

( * ) Notice: Subject to any disclaimer, the term of this patent is extended or adjusted under 35 U.S.C. 154(b) by 0 days.

(21) Appl. No.: 15/888,801

(22) Filed: Feb. 5, 2018

(65) Prior Publication Data
US 2018/0231449 A1    Aug. 16, 2018

(30) Foreign Application Priority Data

Feb. 15, 2017    (DE) .................. 10 2017 001 438

(51) Int. Cl.
*G01N 15/06* (2006.01)
*G01N 15/14* (2006.01)
*G01N 15/10* (2006.01)
*G01N 15/00* (2006.01)

(52) U.S. Cl.
CPC ......... *G01N 15/06* (2013.01); *G01N 15/1425* (2013.01); *G01N 15/1456* (2013.01); *G01N 2015/0046* (2013.01); *G01N 2015/0693* (2013.01); *G01N 2015/1068* (2013.01); *G01N 2015/1486* (2013.01)

(58) Field of Classification Search
CPC ............ G01N 15/0211; G01N 1/2247; G01N 2015/0046; G01N 15/0656; G01N 15/1434; G01N 1/22; G01N 21/53; G01N 15/0205; G01N 29/036; G01N 15/06; G01N 15/1425

USPC ............................................ 356/335–343, 73
See application file for complete search history.

(56) References Cited

U.S. PATENT DOCUMENTS

| | | | | |
|---|---|---|---|---|
| 4,449,816 A | * | 5/1984 | Kohsaka | G01N 15/065 356/336 |
| 2003/0016357 A1 | * | 1/2003 | Shofner | G01N 15/0211 356/337 |
| 2009/0039249 A1 | * | 2/2009 | Wang | G01N 15/0205 250/287 |
| 2010/0134797 A1 | * | 6/2010 | Arakawa | G01N 15/1429 356/338 |
| 2011/0310386 A1 | * | 12/2011 | Renard | G01N 15/06 356/340 |
| 2012/0001619 A1 | * | 1/2012 | Ukai | G01N 15/0656 324/204 |
| 2012/0242328 A1 | * | 9/2012 | Ukai | G01N 33/2835 324/200 |
| 2014/0247450 A1 | * | 9/2014 | Han | G01N 15/0211 356/338 |
| 2017/0184548 A1 | * | 6/2017 | Karakaya | G01N 5/02 |
| 2018/0231448 A1 | * | 8/2018 | Moenkemoeller | G01N 15/1459 |
| 2018/0231454 A1 | * | 8/2018 | Moenkemoeller | G01N 15/06 |
| 2018/0238777 A1 | * | 8/2018 | Janka | G01N 15/0656 |

* cited by examiner

*Primary Examiner* — Hoa Q Pham
(74) *Attorney, Agent, or Firm* — Andrew Wilford (57) ABSTRACT

A particle mass concentration in an aerosol volume can be detected by an optical particle sensor. In order to ensure that different degrees of contamination of the optical particle sensor can be detected by the sensor and can be taken into consideration, the optical particle sensor identifies individual particles at low particle concentrations of up to 1000 particle s/cm$^3$.

2 Claims, 5 Drawing Sheets

PARTICLE SENSOR

FIELD OF THE INVENTION

The invention relates to a particle sensor, by means of which a particle mass concentration in an aerosol volume can be detected.

BACKGROUND OF THE INVENTION

An aerosol is understood to mean particles in liquid or solid phase suspended in air or a carrier gas in the airborne state. The aerosol is considered to be a disperse system formed of solid or liquid particles that are finely distributed in air or a carrier gas.

Aerosols are characterized by single basic features. A single individual aerosol particle is described by three features, specifically shape, size and substance. The aerosol as an accumulation of many individual particles or as a particle collective is described in greater detail by further properties, specifically concentration and particle size distribution.

Optical particle sensors often work with electromagnetic radiations in a wavelength range of from 600 nm to 780 nm.

The wavelength range of 380 nm to 780 nm is also referred to as light, since it lies within the range perceived by the human eye.

Hereinafter, the term "light" will therefore also be used instead of the term "electromagnetic radiation", since the term "light" includes the range of electromagnetic wavelengths usual for optical particle sensors.

A wavelength of approximately 655 nm is often used, since there are very economical laser diodes with this wavelength as a source for the required light.

In order to measure the particle mass concentration, aerosol photometers (APMs) are used, which are also referred to in the technical literature as "light-scattering nephelometers".

Aerosol photometers measure the concentration in a particle collective. The measurement result is the particle mass concentration. This is often specified in mg/m$^3$.

Due to their operating principle, aerosol photometers can be used with particle mass concentrations up to several 100 mg/m$^3$.

Either laser diodes or light-emitting diodes (LEDs) are used as monochromatic light source for aerosol photometers. LEDs are used in economical aerosol photometers. In principle, optical smoke detectors for example fall under the group of aerosol photometers.

In the case of aerosol photometers a zero-point adjustment must be made regularly, since contamination and ambient influences lead to a drift of the zero point.

High-quality aerosol photometers are provided with means so as to be able to perform this zero-point adjustment automatically. To this end, the aerosol is firstly guided through a filter or over a separator, so that there are no longer any detectable particles in the measurement volume. The "correction value" then recorded is stored and subtracted from the photometer measured values in the subsequent aerosol measurements. The difference is then output as the photometer measured value.

When it comes to taking ambient measurements in cities, aerosol photometers are suitable measurement apparatuses. In heavily loaded cities, partial particle mass concentrations of more than 0.4 mg/m$^3$ are sometimes measured.

Another class of optical particle sensors is constituted by optical particle counters (OPCs). These measurement apparatuses also use the effect of light scattering in aerosols. However, in contrast to aerosol photometers, it is not a particle collective that is measured, but instead individual particles. To this end, the optical and electrical requirements are much higher than in the case of aerosol photometers. In the case of an aerosol photometer, the light scattered by thousands of particles is detected. Since, in the case of an optical particle counter, only the light scattered by an individual particle is detected, a much higher sensitivity and/or light intensity is necessary.

The optical measurement volume, which in aerosol photometers can easily be several 100 to 1000 mm$^3$, has to be made much smaller in the case of optical particle counters. If, for example, 1000 particles per cm$^3$ are to be measured error-free with an optical particle counter, the optical measurement volume must be only approximately 0.5 mm$^3$ in size. It is thus ensured that only one particle is ever located in the optical measurement volume, up to a particle number concentration of 1000 particles per cm$^3$. There are approximately 1000 particles per cm$^3$ for example in Shanghai with a PM2.5 air load of 120 μg/m$^3$.

At higher particle number concentrations, what are known as coincidence errors occur.

There are then a number of particles simultaneously in the optical measurement volume. These particles are then detected as an individual particle and are classified in an incorrect size class. This produces errors in the measurement result.

These coincidence errors mean that, in the above-mentioned case, this optical particle counter can no longer be used already from a relatively low load of 120 μg/m$^3$.

Optical particle counters, however, do have some technical advantages with regard to their usable concentration range compared to aerosol photometers.

Optical particle counters do not have a zero-point drift, since a signal shape is assessed rather than a signal value.

Besides the number of particles, the particle size distribution (PSD) can also be detected on the basis of the signal shapes.

Optical particle counters calculate the particle mass concentration in an aerosol by dividing the detected particle sizes into size classes (bins) and measuring the frequency of occurrence for each size class or for each bin. Each size class or each bin is assigned a specific weighting factor, which, multiplied by the frequency of occurrence, gives the particle mass for this size class or for this bin.

If the particle masses of all relevant size classes or bins are added together, this gives the total mass concentration.

In order to calculate PM2.5, the particle masses of all size classes or bins up to a particle size of 2.5 μm diameter are added together.

In order to calculate PM10, the particle masses of all size classes or bins up to a particle size of 10 μm are added together.

Optical particle counters respond in a much more robust manner to changes to the particle size distribution in the aerosol. If the particle size distribution in the aerosol changes towards large particles, the mass is underestimated with aerosol photometers, since the mass of a particle grows with the square of the surface area. The scattered light, however, is linear to the surface.

In the case of optical sensors and particle sensors, there is always a risk of contamination. Aerosol deposits on optically effective surfaces cause changes to the properties thereof. In the case of optical particle sensors, not only do such surfaces include the surfaces of the optical components, but also the surfaces of the measurement chamber and beam dump. In principle, dust particles or other contaminations can become deposited on the above-mentioned optically relevant surfaces and can thus falsify the measurement result of optical particle sensors.

Various methods, processes and procedures are known for reducing this risk of contamination.

For example, the aerosol is conducted through a coarse filter or over a course separator prior to passing through the particle measurement apparatus comprising the optical particle sensor. This, however, results in the need to regularly change or regularly clean this course filter or course separator.

In order to prevent or reduce the contamination of the optics, an additional, filtered airflow is generated as a sheath flow and insulates the optics from the airflow loaded with particles. This is a technically complex approach, which is generally only used in correspondingly high-quality particle measurement apparatuses. Here as well it is necessary to regularly change the filters for the sheath flow. In addition, it is not possible to prevent contaminations that are caused by outgassing, for example of plasticisers formed of plastic components, and that are produced fundamentally during the time in which the particle measurement apparatus is not being used.

In addition, it is possible to coat the optical parts and components with dirt-deflecting nanostructures. The contamination is thus indeed significantly reduced, but is not prevented in principle.

In the automotive field, particle sensors with operating times of up to 15,000 hours are expected. The maintenance of these particle sensors must be limited to a minimum. Typical intervals are for example every two years or every 30,000 km.

Particularly in the case of particle sensors, however, it is very difficult to define a fixed servicing interval. Here, the actual operating conditions of the particle sensor play a large role. If the motor vehicle for example is used in unusually heavily loaded areas, for example in Beijing, it should thus be anticipated that the particle sensor will need to be maintained or serviced much more frequently than in other areas loaded to a lesser extent. The moisture of the medium carrying the aerosol to be measured, in conjunction with the particle load also has a significant influence on the contamination of optical particle sensors. There is thus always the difficulty of carrying out a servicing or maintenance operation at the appropriate time. In addition, due to the temperature differences in a car between the temperature in a measurement chamber and the temperature of the drawn-in airflow, it is possible that optically relevant surfaces will be subjected to condensation. It must be possible to identify this particular case of contamination, since the obtained measured values will not be meaningful.

OBJECT OF THE INVENTION

The object of the invention is therefore to create a particle sensor with which the degree of contamination and the condensation is readily identifiable for diagnosis purposes, wherein, on the basis of the degree of contamination, it should be possible to derive parameters for a mathematically calculated compensation of the errors caused by the contamination. An automatic zero-point adjustment should also be possible.

SUMMARY OF THE INVENTION

The solution to this problem should take into consideration the following aspects and experiences:

Long-term tests with particle sensors have revealed an interesting contamination behavior. Aerosol deposits occur on the optical components, but also on all other optical relevant surfaces in the particle sensor that come into contact with the aerosol. Here, two effects that are firmly linked to one another have been determined. The degree of the link is dependent on the structure and can be reproduced for all particle sensors of a particular design.

The first effect is that aerosol deposits, for example dust, but also water, on optical outlet surfaces lead substantially to a scattering of the electromagnetic wave and only to a small extent to an absorption of the electromagnetic wave. In the event of condensation the modified refractive index has an effect at the surface of the optics exposed to condensation. These effects are used for example by most of the rain sensors currently used as standard in vehicles. Both the absorbed and scattered component of the light reduce the beam intensity in the optical measurement volume. The intensity of the light scattered by a particle in a detector or reflector of the particle measurement apparatus is thus reduced. With given particles, lower intensities are measured and the particles are therefore classified into smaller particle classes. This results in a reduction of the output particle mass concentration.

In the initial uncontaminated case of operation, almost all of the energy of the electromagnetic wave is concentrated in the measurement volume by means of a focusing optics. At the end of the measurement chamber, the reflection of the light beam is largely prevented by means of the light dump of said measurement chamber. In the case of a well designed optical system, the total scattered light component is less than 1%. In turn, only a proportion thereof of approximately 1% is scattered directly onto the photodiode via the surfaces of the measurement chamber. In the case of a well designed optical system, at most 0.01% of the total light energy thus reaches the photodetector in the form of scattered light.

Particles on the optics which increase the scattered light component by 1% thus double the scattered light incident on the photodetector. At the same time, however, the intensity of the light in the measurement volume is reduced only by 1%.

The second effect is that the surfaces of the measurement chamber in the particle sensor are generally colored so that any scattered light is absorbed to the greatest possible extent. In any case, the refractive index of the surfaces is much smaller than the refractive index of the aerosol to be measured.

Deposits of the aerosol on the surfaces thus mean that the scattered light of a light source or a laser of the particle measurement apparatus is reflected in an intensified manner by the surfaces, and thus the part of the scattered light incident on the detector or the reflector increases.

In the case of an aerosol photometer (APM), this effect means that the signal reflected at the surfaces increases the measured value of the photodetector and that the particle measurement apparatus consequently outputs a measured value that is too high.

The only method known for compensating for this effect is the zero-point adjustment. For this purpose, the aerosol is guided over a separator, for example over a HEPA filter, before being passed through the particle measurement apparatus. Thus, there are then no longer any measurable particles in the measurement chamber. The measured value then provided is stored and is subsequently subtracted from all measured values.

Manufacturers of aerosol photometers (APM) recommend performing this zero-point adjustment regularly in order to compensate for the drift effects.

In the case of an optical particle counter (OPC) the measurement result for the particle mass concentration is not adversely affected by the increased incidence of scattered light in the photodetector.

In the case of an aerosol photometer (APM), however, the additional scattered light leads to a partly considerable overestimation of the particle mass concentration.

In order to solve the problem addressed by the invention under consideration of the above aspects, experiences and effects, it is proposed that the particle sensor has a means for identifying individual particles at low particle concentrations, for example up to 1000 particles/cm$^3$.

If the particle sensor is configured as an aerosol photometer (APM), it must be supplemented by these means in order to identify individual particles. The aerosol photometer (APM) in accordance with an advantageous development is then accordingly equipped with an optical particle counter (OPC), wherein, in a valid measurement range of the optical particle counter (OPC), a measured value thereof can be compared with that of the aerosol photometer (APM), and a change in the ratio between the measured value of the optical particle counter (OPC) and the measured value of the aerosol photometer (APM) can be converted into a degree of contamination of the particle sensor. This embodiment of the particle sensor configured as an aerosol photometer indeed signifies an additional design effort, but with long-term operation of the particle sensor provides, on the whole, much more economical advantages on account of a considerable reduction of the maintenance outlay and a higher availability of the particle sensor. Within the valid measurement range of the optical particle counter (OPC), a measured value of the optical particle counter (OPC) always corresponds to exactly one measured value of the aerosol photometer (APM). These measured values are determined by the calibration. Changes in the particle measurement apparatus or in the optical system thereof, for example caused by contamination, then lead inevitably to a change in the ratio between the measured value of the optical particle counter (OPC) on the one hand and the aerosol photometer (APM) on the other hand. The technical solution in this case makes use of the properties of the optical path.

The scattered light is received by the photodetector of the particle measurement apparatus as a constant signal component.

If the particle sensor is configured as an optical particle counter (OPC), it has a means for detecting the static or constant signal component in order to solve the problem addressed by the invention. On account of its measurement principle, a particle sensor configured as an optical particle counter (OPC) always has the precondition, on account of its design, that this means must be provided.

The constant signal component of the measurement signal is normally filtered out from the measurement signal in the case of an optical particle counter (OPC), since this constant signal component does not contain any information relevant for the individual particle measurement. In the case of optical particle counters (OPCs), amplifier stages coupled to AC voltage are therefore used. Amplifier stages of this kind additionally can be produced with a lower economical outlay and in addition work over a relatively wide temperature range, since all input offset voltages and voltage drifts of the electronic components are also filtered out by the AC voltage coupling.

In the case of the embodiment of the particle sensor as an optical particle counter, the invention makes use of the effect that the scattered light component and therefore the constant signal component in the measurement signal changes as a result of a contamination of the optically effective surfaces of the particle sensor.

In accordance with an advantageous development, the means for detecting the static signal component is a DC voltage-coupled amplifier, the input of which is connected to a photodetector of the optical particle counter and the output of which can be scanned and processed by software by means of an analogue/digital converter.

Since the particle sensors used in the automotive field have to work within a wide temperature range, for example of from −40 degrees C. to 85 degrees C., it is particularly advantageous to use a DC voltage-coupled amplifier that has a very small temperature drift, since the changes to the scattered light induced by the contamination and therefore the static or constant signal of the photodetector can be very small.

BRIEF DESCRIPTION OF THE DRAWING

The invention will be explained hereinafter in greater detail on the basis of embodiments with reference to the drawing, in which.

SPECIFIC DESCRIPTION OF THE INVENTION

Figure 1:
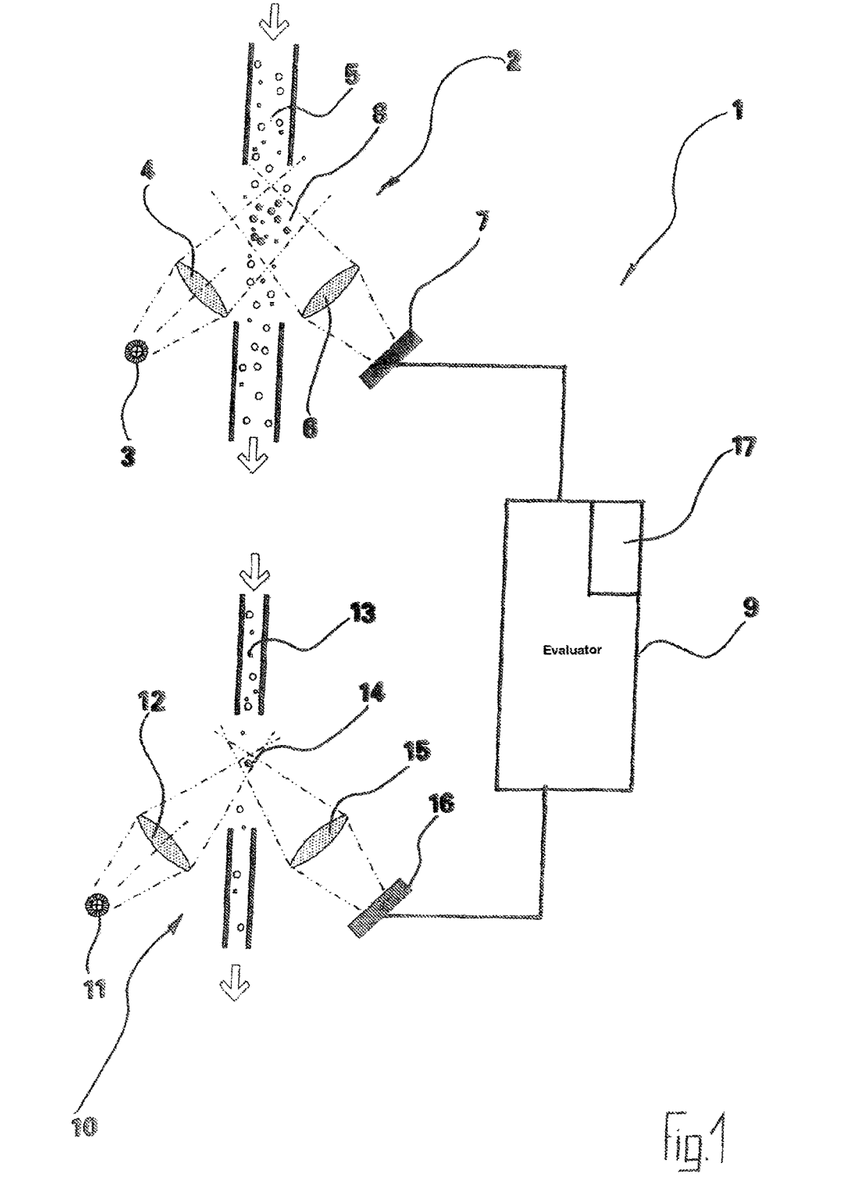
FIG. 1 shows a basic depiction of a first embodiment of a particle sensor according to the invention for determining a particle mass concentration in an aerosol.

A first embodiment of an optical particle sensor 1 according to the invention, shown in a basic depiction in FIG. 1, includes an aerosol photometer (APM) 2, which is used to determine the particle mass concentration in an aerosol.

The aerosol photometer 2 has a monochromatic light source 3, which can be configured as a laser diode or as a light-emitting diode (LED). The light radiation emitted by the monochromatic light source 3 of the aerosol photometer 2 is bundled in an optical lens 4. The light beam leaving the optical lens 4 passes through a gas flow 5, which entrains the aerosol to be measured. Light is reflected in the direction of a further optical lens 6 by particles of the aerosol contained in the gas flow 5. By means of the two optical lenses 4, 6, the measurement volume 8 or the corresponding measurement chamber 8 depicted in principle in FIG. 1 is provided. The light radiation directed in the measurement volume or in the measurement chamber 8 in the direction of the photodetector 7 on account of the particles provided there and bundled by means of the optical lens 6 is detected at the photodetector 7, wherein a photometer measured value corresponding to the detected light radiation is forwarded to an evaluation unit 9 of the optical particle sensor 1.

The photometer measured value forwarded from the photodetector 7 of the aerosol photometer 2 to the evaluation unit 9 corresponds to the particle loading provided or detected in the measurement volume or in the measurement chamber 8.

In the case of the aerosol photometer (APM) 2 of the embodiment shown on the basis of FIG. 1, a great advantage lies in the fact that the measured value detected in the evaluation unit 9 is independent of the flow rate of the gas flow 5 guiding the aerosol to be measured. In the case of the aerosol photometer (APM) 2, the measurement volume is determined by the optical measurement volume.

Furthermore, the optical particle sensor 1 shown in FIG. 1 on the basis of the first embodiment is designed with an optical particle counter 10. The optical particle counter 10 of the optical particle sensor 1 shown in FIG. 1 likewise has a monochromatic light source 11, which can be formed as a laser diode or light-emitting diode (LED). The monochromatic light source 11 emits light radiation, which is bundled in an optical lens 12. The light beam bundled in the optical lens 12 crosses a gas flow 13, which carries the aerosol to be measured. A measurement volume or a measurement chamber 14 of the optical particle counter (10) is significantly smaller than the measurement volume or the measurement chamber 8 of the aerosol photometer 2. This is achieved in the exemplary embodiment, shown in FIG. 1, of the optical particle counter in that the light emitted by the monochromatic light source 11 is focused much more heavily by means of the optical lens 12 than by the optical lens 4 of the aerosol photometer 2. The measurement volume or the measurement chamber 14 of the optical particle counter 10 is dimensioned under consideration of the expectable values of aerosols to be measured, such that merely a single particle of the aerosol is provided therein. The light radiation reflected in the measurement volume or in the measurement chamber 14 of the optical particle counter 10 is directed by an optical lens 15 to a photodetector 16 of the optical particle counter 10 disposed after the optical lens 15 in the beam path. For each individual particle of the aerosol flowing through the measurement volume or the measurement chamber 14 of the optical particle counter 10 together with the gas flow 13, an individual measured value corresponding to the individual particle is thus forwarded at the photodetector 16 of the optical particle counter 10 to the evaluation unit 9 of the optical particle sensor 1. Each individual measured value corresponds to the light reflected by a single particle of the aerosol to be measured and directed by the optical lens 15 to the photodetector 16 of the optical particle counter 10.

In contrast to the aerosol photometer 2 described above, the optical particle counter 10 detects individual particles. Optical particle counters 10 of this kind are used to measure relatively low particle concentrations, for example in interior spaces. Within the scope of their field of application, that is to say at relatively low to average particle number concentrations, which can usually lie between 1,000 and 20,000 particles/cm$^3$, high-quality information with regard to the particle number and the particle size distribution the aerosol is possible by means of optical particle counters 10.

Within the measurement range provided or valid for the optical particle counter 10, a measurement signal of the optical particle counter (OPC) 10 always corresponds to exactly one measurement signal of the aerosol photometer (APM) 2. These measurement signal values are determined on account of the performed calibration.

Changes in the optical particle sensor 1, for example on account of contamination by means of deposited particles, always lead to a change in the ratio between the measurement signal value of the optical particle counter 10 on the one hand and the aerosol photometer 2 on the other hand. This change in the ratio between the two measurement signal values makes it possible to draw conclusions relating to the degree of contamination of the optical particle sensor 1, as can be seen most clearly from FIG. 3, in which the characteristic curves of the aerosol photometer (APM) 2 for an optical particle sensor 1 having no contamination, for an optical particle sensor 1 having light contamination, and for an optical particle sensor 1 having heavy contamination are depicted.

In the case of the above-described embodiment of the optical particle sensor 1, the properties of the optical path are used.

Scattered light, which originates from contaminations of the optical particle sensor 1, is received by the photodetectors 7, 16 as a constant measurement signal component.

The evaluation unit 9 of the optical particle sensor 1 explained above on the basis of FIG. 1 has a functional unit 17, by means of which a degree of contamination of the optical particle sensor 1 can be detected from the processed measurement signal of the aerosol photometer 2 and the processed measurement signal of the optical particle counter 10 and can be taken into consideration when preparing the output value of the evaluation unit 9.

Figure 2:
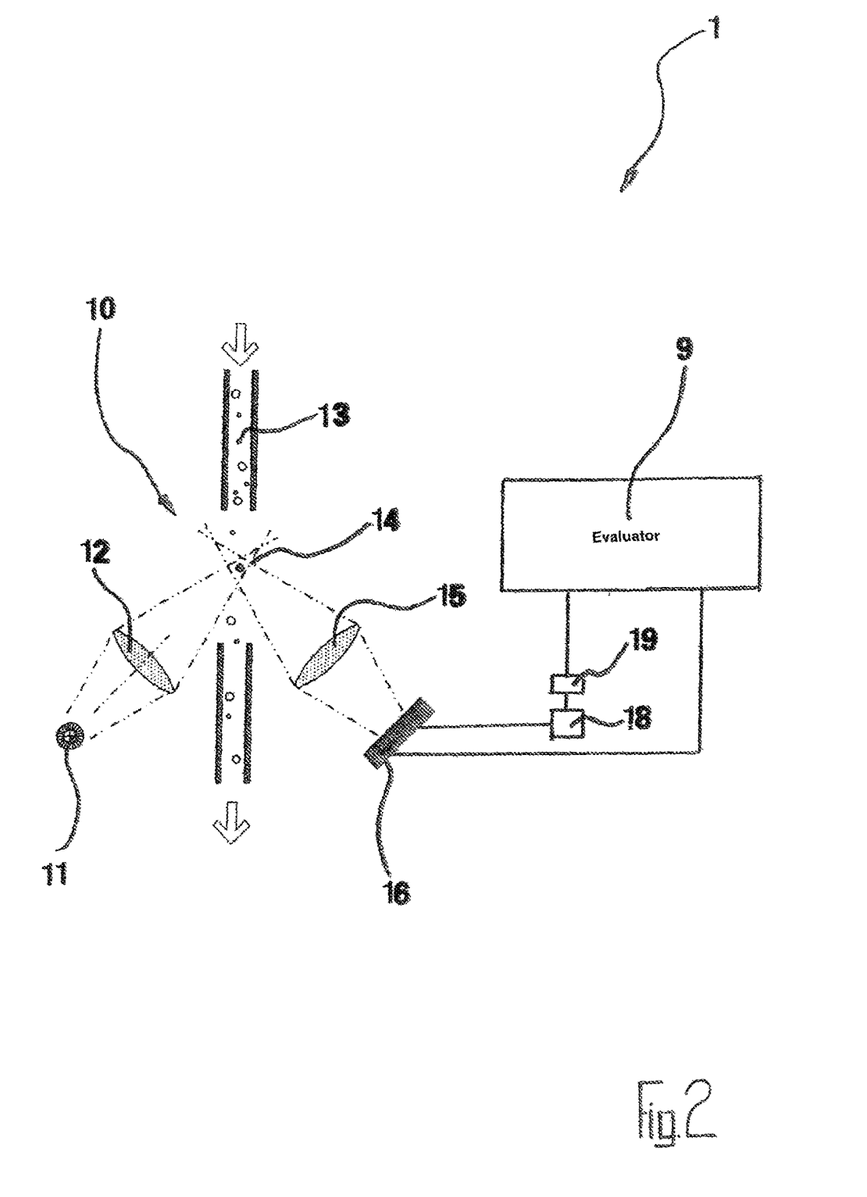
FIG. 2 shows a basic depiction of a second embodiment of the particle sensor according to the invention.

In the case of the embodiment of the optical particle sensor 1 according to the invention shown in FIG. 2, this particle sensor comprises merely the optical particle counter 10 with the monochromatic light source 11, the optical lens 12, the measurement volume or the measurement chamber 14, the optical lens 15 and the photodetector 16, wherein the gas flow 13 flows through the optical particle sensor 1.

Usually, the constant component of the measurement signal of the optical particle counter (OPC) 10 is filtered out from the measurement signal, since it does not contain any information relevant for the individual particle measurement. In the case of optical particle counters 10, AC voltage-coupled amplifier stages are therefore used, although these are not depicted in FIG. 2. AC voltage-coupled amplifier stages of this kind can be produced relatively economically and work over a wide temperature range, since all input offset voltages and voltage drifts of the electronic components are also filtered out as a result of the AC voltage coupling.

In the case of the embodiment of the optical particle sensor 1 according to the invention shown in FIG. 2, the effect that the scattered light component and therefore the constant component in the measurement signal changes with a different degree of contamination of the optical particle sensor 1 or the optically effective surfaces thereof is utilized.

In the case of the optical particle counter 10 of the optical particle sensor 1 shown in FIG. 2, it is therefore provided that the static signal component of the measurement signal of the optical particle counter 10 is determined. In the depicted embodiment a DC voltage-coupled amplifier 18 is used for this purpose, the input side of which amplifier is connected to the photodetector 16 of the optical particle counter 10 and the output side of which is connected via an analogue/digital converter 19 to the evaluation unit 9 of the optical particle sensor 1. Accordingly, the output side of the DC voltage-coupled amplifier 18 is scanned by means of the A/D converter 19 and is then processed by software.

Since optical particle sensors 1 used in a motor vehicle are to be operated in a wide temperature range, for example of from −40 degrees C. to 85 degrees C., it is particularly important to use a DC voltage-coupled amplifier 18 that has a very small temperature drift, since the changes to the scattered light and thus the constant signal component of the measurement signal of the photodetector 16 induced by the contamination can be very small.

Figure 4:
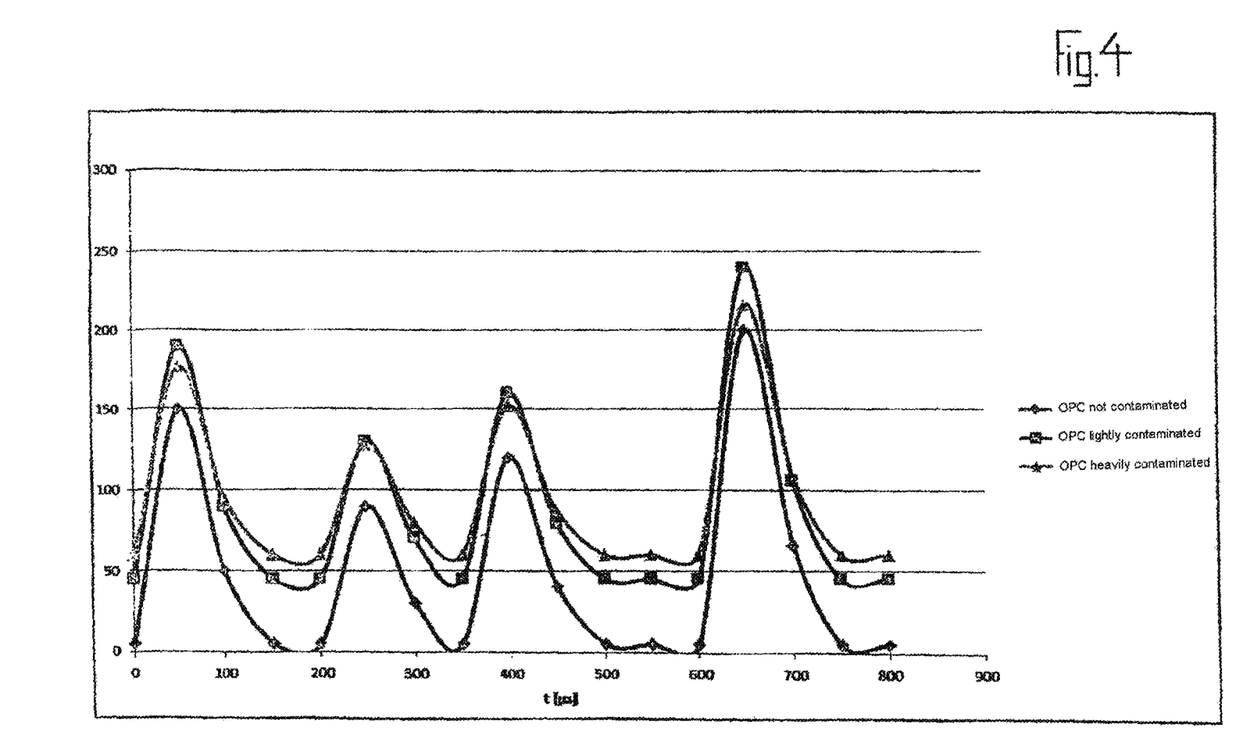
FIG. 4 shows a graph depicting the profile of the signal at the photodetector of an optical particle counter (OPC) with different degrees of contamination.

FIG. 4 shows the signal profile at the photodetector 16 of the optical particle counter 10 with different degrees of contamination. The scattered light caused by contamination leads on the whole to an increase of the measured signal value or the signal level. This offset can be relatively easily determined in the signal profile, since it is the signal level between the particle signals.

This signal value, which is characterizing for the scattered light caused by contamination, is stored and subtracted from the signal value in the following measurements.

With very high degrees of contamination, there is also a small damping of the amplitudes of the particle signals due to the reduced light intensity in the measurement volume, in addition to the signal component caused by the scattered light.

Tests have found that, for a design of the optical particle sensor 1 described above in principle, the link between signal increase and amplitude reduction is a typical characteristic curve.

Since this characteristic curve is determined experimentally for the design in question of the optical particle sensor 1 and is stored in the evaluation unit 9 of the optical particle sensor 1, the amplitude damping factor d belonging to the signal increase can be read in a software-controlled manner from an allocation table and can be used for correction of the measurement signal.

Here:
$s(t)$=photodetector signal at the moment in time t
$h(t)$=the offset value currently stored at the moment in time
$d(t)$=the amplitude damping factor d allocated in the allocation table to the offset h Thus, the corrected measurement signal m is $m(t)=(s(t)-h(t))*d(t)$ In FIG. 5 the signal profile at the photodetector 7 of the aerosol photometer 2 with different degrees of contamination is shown, wherein the unit of time should be noted.

Figure 5:
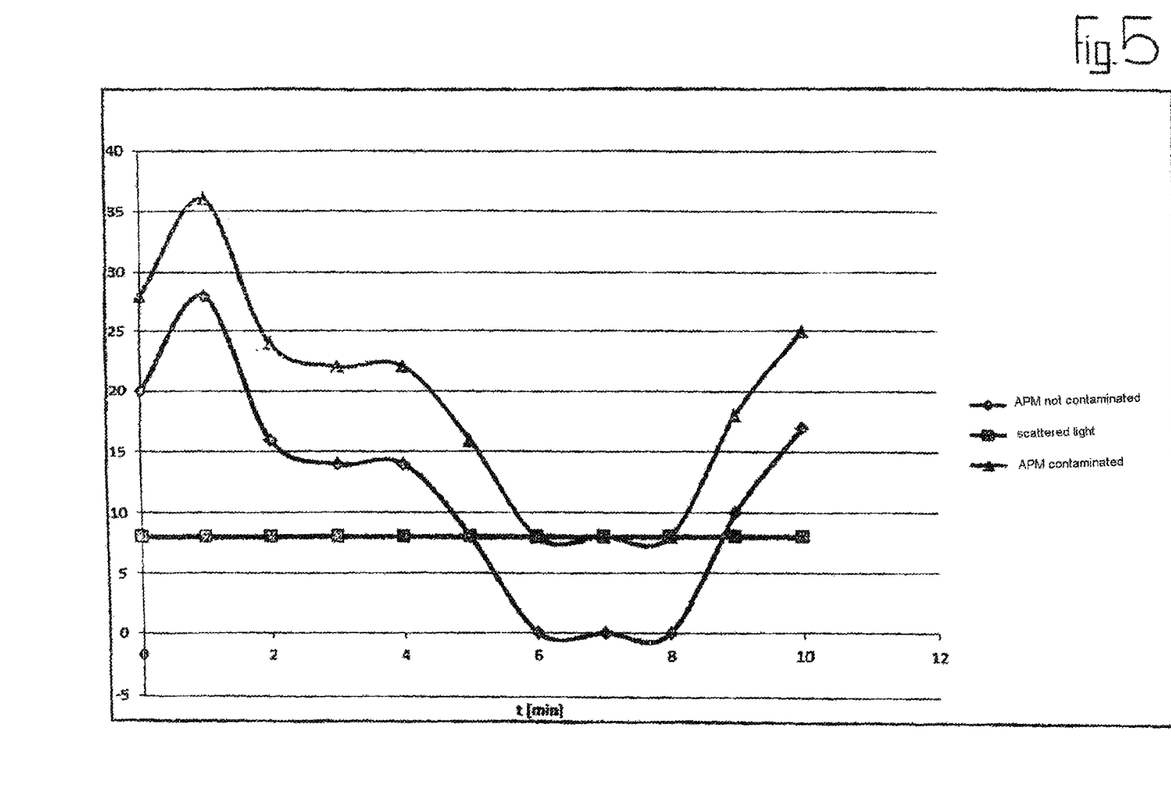
FIG. 5 shows a graph depicting the profile of the signal at the photodetector of an aerosol photometer (APM) with different degrees of contamination.

It is not possible to conclude the degree of contamination of the optical particle sensor 1 on the basis of the signal profile, since it is at no point ensured that a particle mass concentration of 0.0 µg/m³ occurs. Thus, it is not possible to simply assume the lowest value measured in a defined time interval as 0 µg/m³.

If, for example, a particle mass concentration of 20 µg/m³ occurs as lowest value in a defined time interval and if this value is assumed to be a 0.0 µg/m³ value and is stored for offset correction for following measurements, the measurement results subsequently are output too low by this lowest value of 20 µg/m³.

If the optical particle sensor 1, besides the aerosol photometer 2, additionally comprises the optical particle counter 10, as is shown in FIG. 1, the approach described above for the optical particle counter 10 can also be used in conjunction with the aerosol photometer 2.

The sole precondition for regular adjustment of the correction values, specifically offset h and damping factor d, is that the optical particle counter 10 must be able to measure the particle number concentration in a manner free from coincidence errors. With a multi-channel optical particle sensor 1, this can also be enforced in that a switch is made to a channel with a low particle number concentration for the regular adjustment of the correction values.

Since the process of contamination of the optical particle sensor 1 as a result of aerosol deposits is a slowly progressive process, which leads over weeks rather than hours to significant changes of the measurement or output signals, the likelihood of a regular possibility of adjustment of the correction values is relatively high.

If the aerosol photometer 2 and the optical particle counter 10 are separated with regard to the measurement device associated therewith, the correction values determined as described above (offset h and amplitude or level damping factor d) are not applied directly to the measurement signal of the aerosol photometer 2.

Here, the following approach is proposed:

In the case of particle mass concentrations in the measurement range of the optical particle counter 10, the value of the particle mass concentration determined by means of the optical particle counter 10 and the value of the particle mass concentration, determined at the same time by means of the aerosol photometer 2, for different particle mass concentrations are stored. Two value pairs are required, by means of which a straight line can be mathematically calculated. The greatest possible distance between the two value pairs is advantageous.

Figure 3:
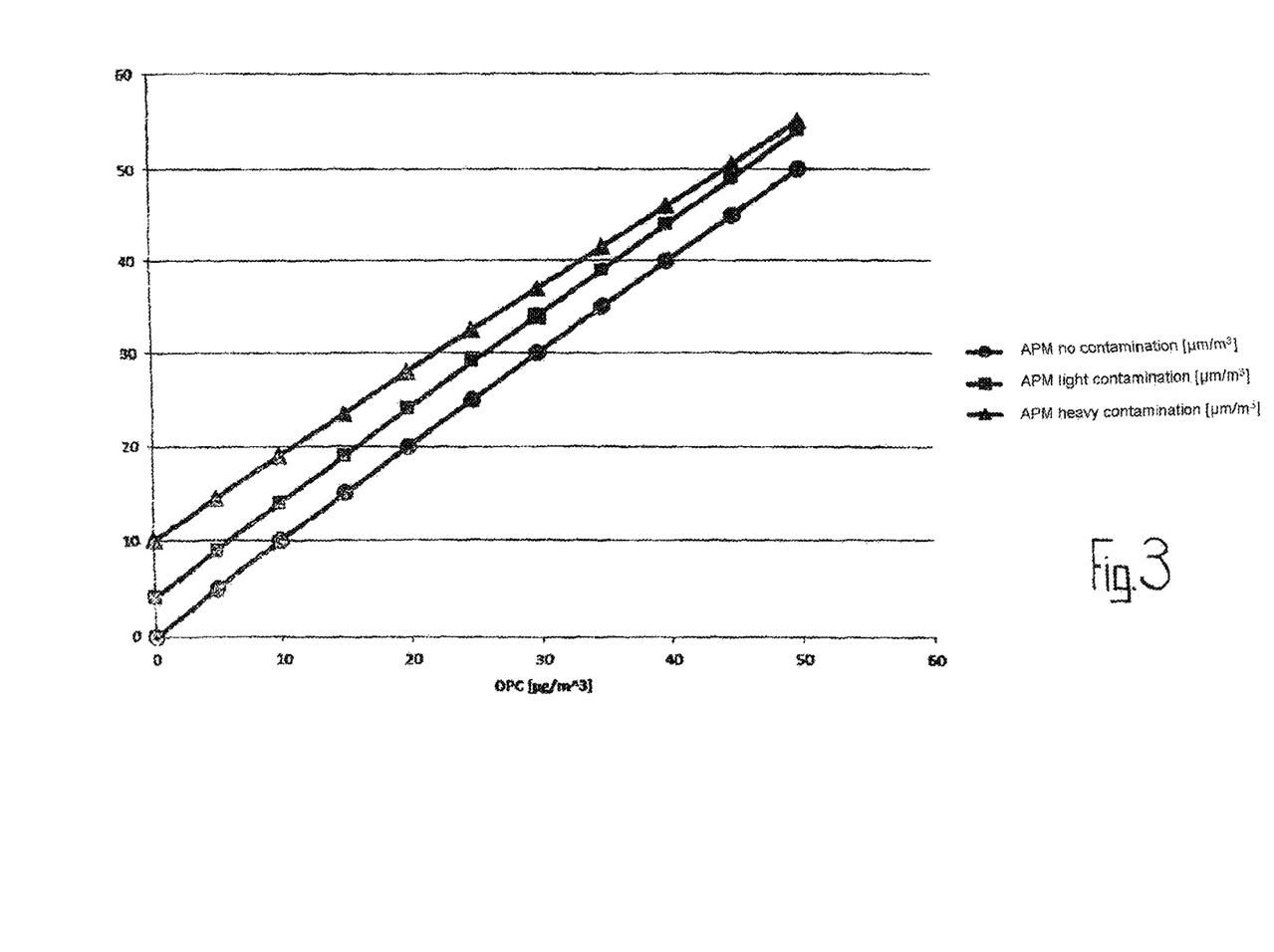
FIG. 3 shows a graph depicting the characteristic curve of an optical particle counter (OPC)/aerosol photometer (APM) with different degrees of contamination.

The method thus to be carried out will be explained hereinafter on the basis of FIG. 3.

The characteristic curve with the circles shows the relationship between the measured value pairs when the optical particle sensor 1 is clean.

There is no offset h and no amplitude damping in the measured value of the aerosol photometer 2.

An offset h means that the straight line plotted between the value pairs intersects the y-axis at the point x=0, not at y=0. The value for y resulting at x=0 corresponds to the offset h.

The gradient of the determined straight line in the clean state of the optical particle sensor 1 has the value 1. In FIG. 3 it is shown that the gradient of the straight line reduces with heavier contamination of the optical particle sensor 1. This is due to the reduction of the light intensity in the measurement volume as a result of the absorption of the light at the contaminated optical outlet and inlet surfaces.

The gradient of the straight line corresponds to the level damping factor p to be applied.

This results in the following function for the correction of the measured values of the aerosol photometer (APM) 2.
$s(t)$=APM photodetector signal at the moment in time (t)
$h(t)$=the offset value currently stored at the moment in time t
$p(t)$=the last line gradient determined This results in the corrected measurement signal m $m(t)=(s(t)-h(t)/p(t)$ A status value for the degree of contamination of the optical particle sensor 1 and thus for the signal quality is generated from the determined correction values. This status value can be queried externally, for example via a diagnosis connection.

In accordance with the degree of contamination of the optical particle sensor 1 determined in the manner described above, it can then be easily decided whether it is necessary to clean or service the optical particle sensor 1.

In the case of an optical particle sensor 1 that has merely one optical particle counter 10 and that is depicted in FIG. 2, only the value for the offset h and the value d for the level damping can be output.

In the case of an optical particle sensor 1 that has both the aerosol photometer 2 and the optical particle counter 10 and that is depicted in FIG. 1, four values can be output on account of the separate measurement systems.

In the case of the optical particle sensors 1 according to the invention, the provided offsets and damping values should advantageously be transformed into a single status value, which for example assigns the signal quality of the optical particle sensor 1 a value between 0 and 100.

Here, it is proposed to use the greater of the two determined offset values in order to generate the status value.

The transformation can be performed for example in accordance with the following calculation rule:

status (0 . . . 100) with 100=very good and 0=very poor.

The offset is recalculated into a particle mass equivalent Ä in µg/m³. In a new system this is 0.0 µg/m³.

Status=100Ä when Ä=100

Status=0 when Ä>100

With the above-described embodiments of optical particle sensors 1, an automatic diagnosis can be provided for identifying degrees of contamination and condensation of an optical measurement path.

The invention claimed is:

1. A particle sensor for detecting a particle mass concentration in an aerosol volume, the particle sensor comprising:

- a light source for irradiating a sample of the aerosol with light that is scattered by the sample;
- an aerosol photometer for identifying individual particles at low particle concentrations up to 1000 particles/cm³;
- an optical particle counter for detecting a static signal component;
- a DC voltage-coupled amplifier for detecting the static signal component and having an input;
- a photodetector connected to the input and emitting an output; and
- an A/D converter loaded with software for scanning and processing the output.

2. The particle sensor according to claim 1, wherein the DC voltage-coupled amplifier has a very small temperature drift.

* * * * *